United States Patent [19]

Arnett et al.

[11] 4,204,069

[45] May 20, 1980

[54] REDUCTIVE ALKYLATION

[75] Inventors: Carroll D. Arnett, Durham, N.C.; Jeremy Wright, Baltimore; Nicolas Zenker, Lutherville, both of Md.

[73] Assignee: Merck & Co., Inc., Rahway, N.J.

[21] Appl. No.: 869,970

[22] Filed: Jan. 16, 1978

Related U.S. Application Data

[62] Division of Ser. No. 747,661, Dec. 6, 1976, Pat. No. 4,082,847.

[51] Int. Cl.² .......................................... C07D 235/08
[52] U.S. Cl. ................................................... 548/325
[58] Field of Search .......................................... 548/325

[56] References Cited

U.S. PATENT DOCUMENTS

| | | | |
|---|---|---|---|
| 3,402,203 | 9/1968 | Tindall | 260/585 C X |
| 3,448,153 | 6/1969 | Cavitt et al. | 260/585 C X |
| 3,954,871 | 5/1976 | Buu-Hoi et al. | 260/570.6 |

OTHER PUBLICATIONS

Adams et al., Organic Reactions, vol. IV, John Wiley & Sons, Inc., New York (1948), pp. 175-177, 181-187 & 196-198.
Emerson et al., Journal of the American Chemical Society, vol. 60 (1938), p. 2024.

Primary Examiner—Richard Raymond
Attorney, Agent, or Firm—Daniel T. Szura

[57] ABSTRACT

1(5-benzimidazolyl)-2-isopropylaminoethanol, pharmaceutically acceptable salts thereof, and their preparation are disclosed. These compounds have pharmaceutical utility e.g. as broncholidators.

3 Claims, No Drawings

REDUCTIVE ALKYLATION

This is a division of application Ser. No. 747,661, filed Dec. 6, 1976, now U.S. Pat. No. 4,082,847.

BACKGROUND OF THE INVENTION

The present invention is concerned with novel benzimidazole substituted aminoethanols, their preparation and pharmaceutical use.

Isoproterenol is a dihydroxyphenylisopropylaminoethanol having the formula

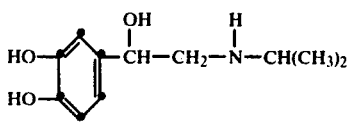

Isoproterenol has valuable bronchodilator properties and is used clinically for treating asthma. Isoproterenol is also known to reduce intraocular pressure. However, isoproterenol also exhibits undesirable cardiovascular side effects such as palpitations, tachycardia and the like.

R,S-1-(5-benzimidazolyl)-2-aminoethanol is a known compound.

A novel compound, 1-(5-benzimidazolyl)-2-isopropylaminoethanol has been discovered. The compound has good bronchodilator activity, and can be used to reduce intraocular pressure, with a reduced tendency to cause the undesirable cardiovascular side effects.

SUMMARY OF THE INVENTION 1-(5-benzimidazolyl)-2-isopropylaminoethanol, its salts, their preparation and use as pharmaceutical agents.

PREFERRED EMBODIMENTS

A preferred embodiment of the present invention is compounds having the formula

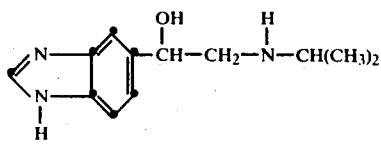

and pharmaceutically acceptable salts thereof. The formula I compound bears an asymmetric carbon atom and thus is optically active. The compound includes the individual isomers as well as the racemate and other isomer mixtures.

Various symbols are used to designate the optical isomers such as l and d, (−) and (+), L and D and combinations thereof. In addition, there are the stereospecific designations, sinister (S) and rectus (R); these symbols or terms indicate the actual spatial configuration of the particular isomers.

The appropriate isomer designation will be used in naming compounds. Where no designation is given, the individual optical isomers and mixtures are considered to be included.

Pharmaceutically acceptable salts of the compounds of formula I are ordinarily salts of the free base with any useful acid. These acids include inorganic as well as organic acids. Examples of suitable inorganic acids are the hydrohalides e.g. HCl, HI, HBr, sulfuric acid, phosphoric acid and the like. Organic acids include carboxylic acids as well as non-carboxylic acids. Carboxylic acids having 2 to about 24 carbon atoms are useful. Examples of such acids are acetic acid, pamoic acid, maleic acid, tartaric acid, citric acid, hexanoic acid, oleic acid, succinic acid, palmitic acid, fumaric acid, malic acid, oxalic acid and the like. An example of an especially useful non-carboxylic acid is isethionic acid.

The compounds of the present invention have activity as bronchodilators and ocular hypertension reducers, having a reduced tendency to cause undesirable cardiovascular side effects such as tachycardia, palpitations and the like. The bronchodilator activity makes the compounds useful for treating pulmonary conditions such as asthma. Their ability to reduce elevated intraocular pressure (ocular hypertension) makes the compounds useful for treating certain eye diseases such as wide angle glaucoma.

For use as bronchodilators, the present compounds can be administered to a patient in any suitable dosage form e.g. inhalation powder, aerosol, parenteral solution, spray solution, tablets, etc., via any suitable route e.g. orally (inhalation, sublingually etc.) or parenterally (subcutaneously, intramuscularly etc.). The oral route is preferred and inhalation is most preferred. The total daily dosage may be varied and can range from about 5–100 milligrams of compound I per kilogram of body weight.

For reducing elevated intraocular pressure, the compounds of the present invention are instilled into the eye of the patient. These compounds may conveniently be administered in ophthalmic solutions. Ophthalmic solutions, as defined in the National Formulary, are sterile solutions, essentially free from foreign particles and suitably compounded and dispensed for instillation into the eye. The concentration of the present compound in such solutions is varied. Useful solutions can contain from 0.1% to about 10% by weight of the present compound. Solutions containing 1, 1.5, 2.5 and 5% may be conveniently used.

In addition to the ophthalmic solution dosage form, the present compounds may also be administered to the eye by means of physiologically compatible insert which serves as a carrier and continuous dispenser of said compound. The composition of this insert and the amount of formula I compound it carries may be varied depending on the physico-chemical characteristics of the insert, the dispensing rate desired, the activity of the particular compound etc.

Pharmaceutical activity resides in the individual optical isomers as well as in the racemates and isomer mixtures.

The pharmaceutical activity of the present compounds was determined in vitro using conventionally isolated tissue preparations (guinea pig atrial and tracheal strips). The atrial strips were used to demonstrate the effect of the present compounds, and isoproterenol, on the β-1 adrenergic receptors. Both chronotropic (rate) and inotropic (force) responses were thereby assessed. The tracheal strips were used to demonstrate the effect of the present compounds and isoproterenol on the β-2 adrenergic receptors. The observed effect on tracheal muscle relaxation is equated with and considered to be an indication of bronchodilator activity. The β-1 and β-2 adrenergic receptor designations are those of Lands et al., Nature, 214, page 597 (1967).

The results obtained in these in vitro evaluations of pharmaceutical activity are presented in the following table:

Table I

Comparison of the Guinea Pig $\beta$-Receptor Agonistic Activity of R, S-1[5-Benzimidazolyl]-2-isopropylaminoethanol (R, S-BENZISO) with the Activity of the Known Agonist R,S-Isoproterenol (R, S-ISO).

|  | R, S-ISO [1] | R, S-BENZISO [2] |
|---|---|---|
| Atrial rate ($\beta$-1) | | |
| pD$_2$[b] | $7.66 \pm 0.13$ (6)[a] | $5.21 \pm 0.08$ (5) |
| relative activity[c] | 100 | 0.355 |
| % maximum response[d] | | $50 \pm 9$ |
| Atrial force ($\beta$-1) | | |
| pD$_2$ | $\frac{7.87 \pm 0.10}{100}$ (6) | $5.42 \pm 0.20$ (3) |
| relative activity | | 0.355 |
| % maximum response | | $33 \pm 12$ |
| Tracheal relaxation ($\beta$-2) | | |
| pD$_2$ | $\frac{7.10 \pm 0.09}{100}$ (5) | $5.78 \pm 0.08$ (4) |
| relative activity | | 4.79 |
| % maximum response | | $58 \pm 7$ |
| Ratio, $\beta$-2/$\beta$-1[e] | — | 13.5 |

[a] values are means $\pm$ S.E.M. with the number of experiments in parentheses.
[b] pD$_2$ = negative logarithm of ED$_{50}$.
[c] relative activity = [ED$_{50}$ (R,S-ISO/ED$_{50}$ (R,S-BENZISO)] $\times$ 100.
[d] % maximum response = [maximum response (R,S-BENZISO)/maximum response (R, S-ISO] $\times$ 100.
[e] ratio, $\beta$-2/$\beta$-1 = relative activity (tracheal relaxation)/relative activity (artrial rate).
[1] administered as the hydrochloride
[2] administered as the dihydrochloride, M.P. = 217° C.

The data in table I clearly indicate that the present compound (R,S-Benziso) has good bronchodilator activity ($\beta$-2)—and while it is also a cardiac stimulant ($\beta$-1 force and rate) the $\beta$-2/$\beta$-1 ratio (13.5) indicates that the present compound is more bronchodilator selective than is isoproterenol. Accordingly, undesirable side effects such as tachycardia, would be reduced when the present compounds are utilized as bronchodilators.

In a similar manner, it is expected that the present compounds, when used to reduce elevated intraocular pressure, will have a lesser tendency to cause the aforesaid undesirable cardiac side effects.

R,S-1(5-benzimidazolyl)-2-isopropylaminoethanol was also found to decrease blood pressure of a rat when injected intravenously.

The present compounds may be used as free amines or as pharmaceutically acceptable salts, with salts being more commonly used.

The compounds of the present invention can be prepared by any suitable process. An especially useful process for preparing these compounds is by the reductive alkylation of the corresponding benzimidazole-aminoethanol. This alkylation is illustrated by the following equation.

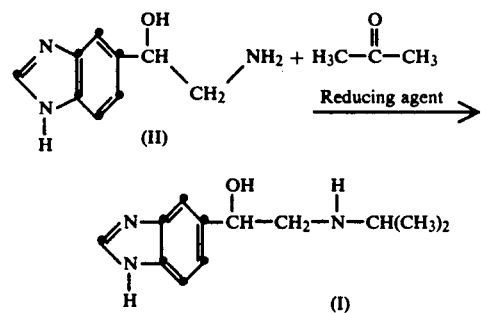

Conventional reductive alkylation reaction conditions are utilized, see e.g. Organic Reactions IV, ed. by Roger Adams (New York; John Wiley & Sons Inc.) p. 197 (1948).

While various reducing agents may be used, an especially useful system is hydrogen in the presence of a suitable catalyst. A preferred catalyst is palladium on charcoal. An inert liquid reaction medium such as an alkanol (methanol, ethanol and the like) is ordinarily used. In addition, it has been found that the presence of anhydrous Na$_2$SO$_4$ improves the yield of the formula I product.

The following example illustrates the preparation of the formula I compound and intermediates. Parts are by weight and temperatures are centigrade unless otherwise indicated.

EXAMPLE 1

A. 3-Nitro-4-formamidobenzaldehyde

To 56.6 ml (1.50 mol) of HCOOH was added 24.9 g (150 mmol) of 3-nitro-4-aminobenzaldehyde. The solution was heated to reflux, 28.4 ml (300 mmol) of acetic anhydride was added dropwise and the solution was refluxed for 30 minutes. The resulting suspension was cooled and poured into 400 ml of cold H$_2$O with rapid stirring. The product was filtered, air dried, and recrystallized from isopropanol to yield 23.2 g (80%) of 3-nitro-4-formamidobenzaldehyde as a bright yellow powder: melting point=183°–191°.

B. R,S-1-(3-Nitro-4-formamidophenyl)-2-nitroethanol

To 23.8 ml of 25% NaOCH$_3$ in MeOH (110 mmol of NaOCH$_3$) and 250 ml of 1,4-dioxane was added 27.0 ml (500 mmol) of CH$_3$NO$_2$ (96%). The suspension was stirred at 0° (ice bath) during the addition of 19.4 g (100 mmol) of 3-nitro-4-formamidobenzaldehyde. After 1 hour, 6.3 ml (110 mmol) of acetic acid in 50 ml of 1,4-dioxane was added, the suspension stirred for 10 min. and filtered. The solvent was evaporated under vacuum and the product recrystallized from CHCl$_3$ to yield 7.9 g (31%) of R,S-1-(3-nitro-4-formamidophenyl)-2-nitroethanol as a bright orange crystalline solid; melting point=129°–131°.

C. R,S-1-(5-Benzimidazolyl)-2-aminoethanol.HCl

To 2.0 of anhydrous Na$_2$SO$_4$ in 200 ml of isopropanol was added 2.0 g (7.8 mmol) of R,S-1-(3-nitro-4-formamidophenyl)-2-nitroethanol, followed by 2.0 g of 5% Pd/C. The mixture was reduced at 2.8 kg/cm$^2$ of H$_2$ for 16 hr. in a steam-jacketed bottle. The solution was cooled and filtered to remove the catalyst. The solvent was evaporated under vacuum and the product converted to its dihydrochloride salt by the addition of 10 ml of 4 N HCl. After evaporating excess H$_2$ under vacuum, the solid was recrystallized from 95% EtOH to yield 600 mg (30%) of R,S-1-(5-benzimidazolyl)-2-aminoethanol as its dihydrochloride salt: melting point =248° (dec.).

D. R,S-1-(5-benzimidazolyl)-2-isopropylaminoethanol.2HCl

To 625 mg (2.5 mmol) of R,S-1-(5-benzimidazolyl)-2-aminoethanol.2HCl in 20 ml of H$_2$O was added 14 g of Amberlite IR-45 ion exchange resin (hydroxide form). The suspension was filtered after 10 min. and the H$_2$O evaporated under vacuum to yield 426 mg (96%) of R,S-1-(5-benzimidazolyl)-2-aminoethanol, as the free base. To this light yellow oil in 50 ml of CH$_3$OH was added 500 mg of anhydrous Na$_2$SO$_4$ and 3.7 ml (50 mmol) of acetone, followed by 500 mg of 10% Pd/C. The mixture was reduced at 2.8 kg/cm$^2$ of H$_2$ for 2 hr. in a steam-jacketed bottle. The solution was cooled and filtered to remove the catalyst. The solvent was evaporated under vacuum and the R,S-1-(5-benzimidazolyl)-2-isopropylaminoethanol converted to its dihydrochloride salt by the addition of 10 ml of 4 N HCl. After evaporating excess H$_2$O under vacuum, the product was triturated in 200 ml of refluxing acetone for 1 hour, cooled, and filtered to yield 213 mg (29%) of R,S-1-(5-benzimidazolyl)-2-isopropylaminoethanol dihydrochloride: melting point=211° (dec.).

When, instead of triturating in acetone, dihydrochloride salt was recrystallized from isopropanol, the recrystallized R,S-1-(5-benzimidazolyl)-2-isopropylaminoethanol dihydrochloride obtained had a melting point of 217° C. (dec).

The free amine product prepared in Example 1 is the racemate (R,S). If desired, the racemate can be separated into its individual isomers using conventional resolution techniques.

Other salts of R/S,R or S-1-(5-benzimidazolyl)-2-isopropylaminoethanol can be prepared by appropriate treatment of the free amine with the desired acid or acid source e.g. acyl halide or anhydride.

Claims to the invention follow.

What is claimed is:

1. A process for preparing a compound having the formula

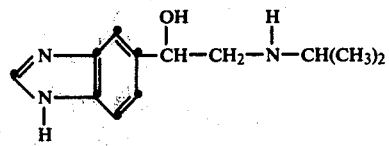

which comprises the reductive alkylation of a compound having the formula

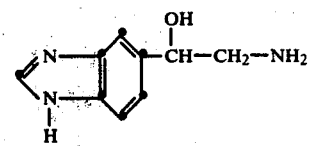

with acetone in the presence of anhydrous Na$_2$SO$_4$.

2. The process of claim 1 wherein said alkylation is carried out in the presence of hydrogen and a suitable catalyst.

3. The process of claim 2 wherein said catalyst is palladium on charcoal.

* * * * *